United States Patent [19]

Rhine et al.

[11] 4,194,513
[45] Mar. 25, 1980

[54] ANTENATAL CELL EXTRACTING DEVICE AND METHOD

[75] Inventors: Samuel A. Rhine, Concord, Mass.; Joseph F. Thompson; Catherine G. Palmer, both of Indianapolis, Ind.

[73] Assignee: Indiana University Foundation, Bloomington, Ind.

[21] Appl. No.: 793,914

[22] Filed: May 5, 1977

[51] Int. Cl.² .............................................. A61B 10/00
[52] U.S. Cl. .................................................... 128/750
[58] Field of Search ............. 128/2 B, 2 W, 2 F, 344, 128/349, 214.4, 750-759, 240; 27/24 A, 24 R

[56] References Cited

U.S. PATENT DOCUMENTS

| 396,754 | 1/1889 | Mayfield | 128/349 R |
|---|---|---|---|
| 2,156,522 | 5/1939 | Bowmer | 27/24 A |
| 3,173,414 | 3/1965 | Guillont | 128/2 B |
| 3,438,366 | 4/1969 | Kariher et al. | 128/2 B |
| 3,636,940 | 1/1972 | Gravlee | 128/2 B |
| 3,777,743 | 12/1973 | Binard et al. | 128/2 B |
| 3,851,647 | 12/1974 | Monestere et al. | 128/214.4 |
| 3,861,393 | 1/1975 | Durand | 27/24 A X |

FOREIGN PATENT DOCUMENTS 257747  3/1965  Australia ................................. 128/2 B

OTHER PUBLICATIONS

"Fetal Sex Prediction by Sex Chromation of Chorionic Villi Cells During Early Pregnancy", Chin. Med. Jrnl. 1(2):1(7-126, Mar. 1975.
Langman, Jan "Medical Embryology", Williams & Wilkins, Baltimore, 1969 pp. 30-33, 40-41, 44-45, 69-83.

Primary Examiner—Robert W. Michell
Assistant Examiner—Francis J. Jaworski
Attorney, Agent, or Firm—Kirkland & Ellis

[57] ABSTRACT

This application discloses an antenatal cell extracting device comprising a thin, flexible, plastic tube adapted for cervical insertion in a human female. A flexible closure is provided at the proximal end of the plastic tube, and passing through the flexible closure, the plastic tube and the distal end of the tube is a plunger. A valve in the form of a smooth ball, the diameter of which is greater than the diameter of the tube, is fixed to the end of the plunger, and, upon reciprocating movement of the plunger with reference to the tube, the valve is caused to open and close. Means are provided for causing fluid to flow through the tube when the valve is opened, such means, preferably taking the form of a syringe connection to the flexible closure.

7 Claims, 3 Drawing Figures

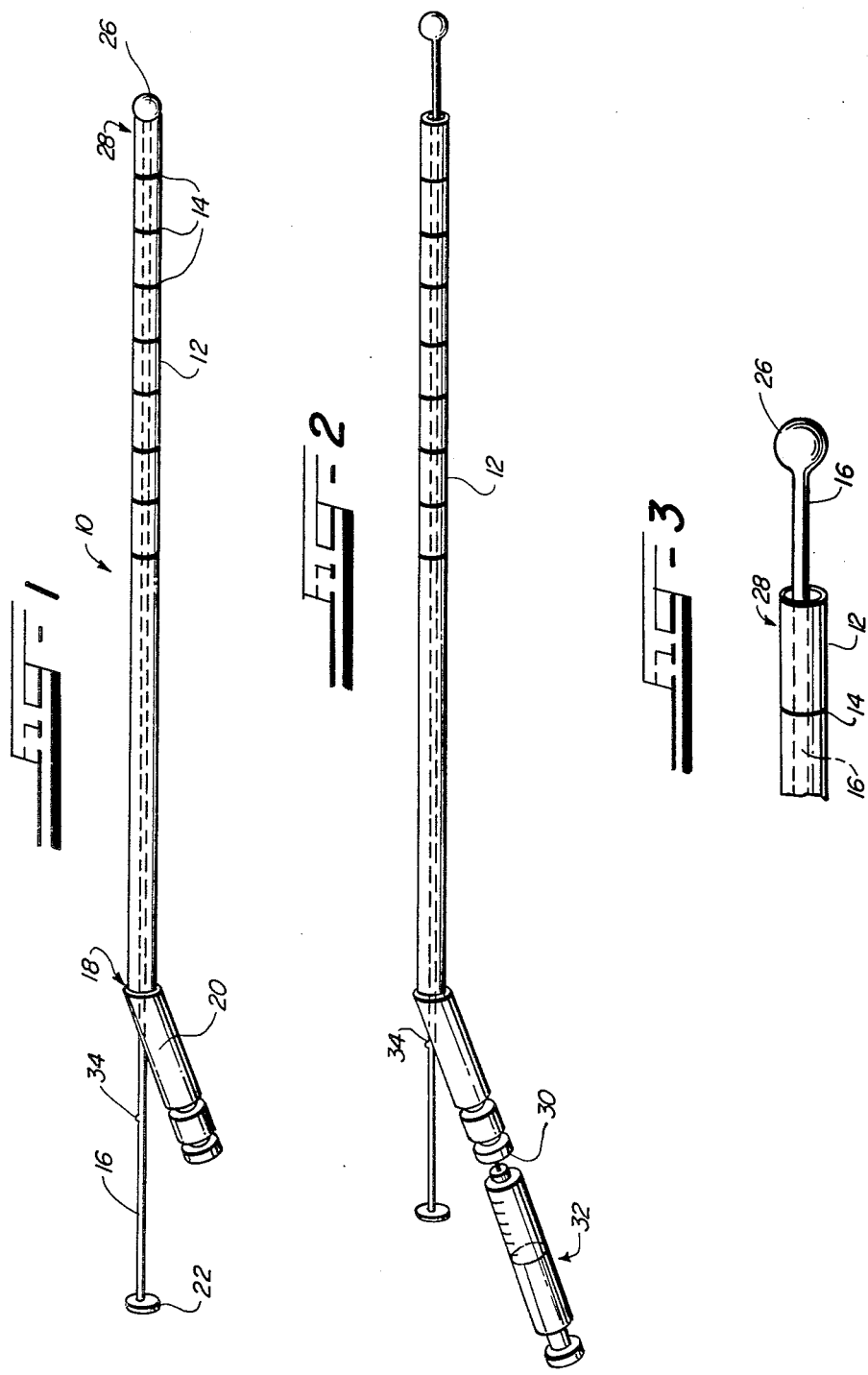

ANTENATAL CELL EXTRACTING DEVICE AND METHOD

BACKGROUND OF THE INVENTION

1. Field of the Invention

This invention relates to obstetric device and methods and more particularly to a safe, sterile device that may be employed to obtain samples of exfoliated fetal tissue from the uterine cavity.

2. Description of the Prior Act

The obstetric arts have long sought a safe, simple, method applicable on a mass basis to obtain sample tissue during pregnancy in order to permit prenatal diagnosis of genetic diseases. Amniocentesis is the method now employed to perform such prenatal diagnoses. This method, which involves securing a sample of the amniotic fluid, has several disadvantages. In addition to the undesirable aspect of requiring that the abdominal wall, uterus, and amniotic membrane be permeated with a needle in order to obtain the sample, the procedure cannot be employed until the fetus has reached a certain size, thereby ruling out first trimester screening.

Thus, the current state of the art does not provide a device or method that can be used for first trimester screening of pregnant females in order to identify fetuses developing with a chromosomal disorder.

A variety of devices have been suggested for gynecological use to sample vaginal, cervical or uterine tissue for the presence of cancer cells. Such devices are designed to obtain tissue samples which are then fixed (killed and preserved) onto glass slides for examination by a pathologist under a microscope. In contrast with such a gynecological cell sampling procedure, antenatal cells gathered for genetic examination are not fixed but rather are cultured in an incubator before examination for genetic disorder.

Thus, the prior art gynecological tools have been designed without regard for contamination by bacteria (since bacteria would be killed during the cell fixing practice in any case). In contrast, with antenatal cells, the presence of even a single bacterium cell in the fetal tissue culture could destroy the entire specimen, and thus maintenance of sterility is the quintessence of a satisfactory antenatal cell extracting method and device.

As noted, the prior art gynecological cell sampling devices have as their objective the obtaining of sample cells from the female, rather than the accumulation of fetal cells. Since the gynecological tools as described were designed to be used in a non-pregnant reproductive tract, they have been designed without regard for the importance of avoiding any effect on the pregnant state of the carrier female. Thus, such gynecological tools have utilized rigid or scratchy projections to scrape or aspirate tissues onto or into the sampling device (See, e.g., U.S. Pat. Nos. 3,838,681; 3,664,328; 3,800,781; and 3,877,464.)

U.S. Pat. No. 3,857,384 inserts a microscope slide so that the cervical specimen is obtained directly as a smear on the slide for cytologic evaluation. U.S. Pat. No. 3,777,743 employs negative suction to draw sample cells into the device for subsequent examination. Such an approach of utilizing negative suction to draw sample cells into the device would be totally unsuited for use in a antenatal cell gathering device because of the danger, particularly during the early stages of pregnancy, that the pregnancy would be adversely affected and indeed, possibly terminated by the use of the procedure.

Accordingly, it is a primary object of this invention to obtain a device for gathering fetal cells during the early stages of pregnancy.

Another object is to provide a device of the character described which may be safely employed without risk of adversely affecting the pregnancy.

A further object is to provide a device of the character described which is sterile and can be used without risk of contamination.

A still further object of the invention is to provide an antenatal cell extracting device which may be employed as a mass screening test for virtually all pregnant mothers during the first trimester of pregnancy in order to diagnose the presence of fetal sex and genetic disease at an early stage.

DESCRIPTION OF THE DRAWING

FIG. 1 is an elevational view of an antenatal cell extracting device in accordance with this invention.

FIG. 2 is a similar view of the device with the valve positioned in an open configuration.

FIG. 3 is a fragmentary enlarged view showing the valve in its open position.

SUMMARY OF THE INVENTION

The foregoing and other objects, advantages, and features of the present invention may be obtained with an antenatal cell extracting device comprising flexible, plastic tube means having proximal and distal ends; closure means provided at the proximal end thereof; plunger means provided within the lumen of the tube means and passing through the closure means at the proximal end of the tube means; valve means provided in combination with the plunger adjacent to the distal end of the tube and adapted, upon reciprocation of the plunger with reference to the tube means, to move from a closed position, wherein the distal end of the tube means is sealed, to an open position wherein the distal end of the tube means is open; and means for causing fluid to flow through tube means when the valve is open.

Such a device is especially adapted to obtain exfoliated fetal cells that collect near the internal os of the uterus during pregnancy. The device is inserted into the cervix of a pregnant female, and the plunger is moved so as to open the distal end of the tube. Sterile isotonic saline solution is caused to gently flow through and into the region surrounding the distal end thereof, and then is drawn gently back into the tube so as to close the valve. The device is then removed, with exfoliated fetal cells drawn back into the tube with the saline solution being carried within the tube.

The device is maintained in a sterilized condition so as to prevent sample contamination, and no scratching, scraping or negative suction is employed to gather the sample. Instead, the injected saline solution first provides a gentle positive pressure and then is drawn back into the sample gathering device as the pressure is restored to its normal condition. Furthermore, the device may be employed without affecting the integrity of the amniotic sac and thus can be utilized early during the pregnancy, more particularly during the first trimester thereof.

DETAILED DESCRIPTION OF THE PREFERRED EMBODIMENTS

In accordance with the present invention, a simple, device is obtained for use in obtaining fetal cell samples during the early stages of pregnancy without affecting the pregnancy itself or causing significant discomfort to the pregnant female. With specific reference to FIG. 1, there is shown an antenatal cell extracting device 10. The device consists of a flexible, thin-walled, plastic tube 12 of suitable length for insertion into the cervix. Any convenient length may be used, but it has been found that a 15 cm. tube is especially useful. The exterior surface of the tube may be provided with indicia such as rings 14 which may be used to gauge the degree of insertion of the tube during use.

Substantially any suitable non-toxic, physiologically inert plastic may be employed in fabricating the tube, but it has been found that material such as polyethylene, polypropylene, nylon, and the like may be satisfactorily employed to fabricate the tube.

Passing through the lumen of the tube, is a plunger 16 that is longer than the tube. The proximal end 18 of the tube is fitted with a flexible closure taking the form of a short flexible tubular sleeve 20, which may be formed of rubber or the like. The plunger 16 passes through the sleeve 20 so as to be movable with respect thereto and with respect to the tube 12. Conveniently, the proximal end of the plunger 16 is formed into a handle 22 which may be grasped by the operator so as to cause the plunger to move reciprocally with respect to the tube. The plunger 16 may be formed of metal such as stainless steel, but other suitable, generally rigid materials may be employed.

The distal end of the plunger 24 has provided thereon a smooth ball 26 which may be formed of non-toxic, physiologically inert plastic. The distal end 28 of the tube 12 cooperates with the ball 26 to provide valve means for opening and closing the interior lumen of the tube to fluid. For this reason, the ball is desirably of a diameter greater than the diameter of the tube 12. Conveniently the ball may be about 3.5 mm in diameter and the tube 12 is about 2.5 mm in diameter.

A syringe adapter 30 is fitted into the sleeve 20, and a syringe, shown generally at 32, may be removably fitted into the adapter 30 in order to provide a source of fluid for a purpose that will hereinafter be described.

The device as shown in FIG. 1 is sterilized before use by autoclaving or gas sterilization. Conveniently, the device may be sterilized upon manufacture and assembly and retained in sterile condition until just prior to use.

In use, the device with the valve in its closed position (i.e., with the ball 26 flush adjacent to the distal end 28 of tube 12) is inserted into the cervix so that the distal end 28 is positioned at the internal os of the uterus. The plunger handle 22 is grasped, and the plunger moved a short distance until a stop means (e.g., a protrusion 34 on the plunger) contacts the sleeve 20, thereby opening the interior lumen of the tube 12 for fluid passage. Using syringe 32, isotonic saline solution is caused gently to flow through the tube and into the region surrounding the distal end of the tube thus creating a slight positive pressure in the uterus. The syringe plunger is then returned to its original position, and the saline solution is drawn back into the interior of the tube as the intra uterine pressure returns to its original level. The saline solution flowing into the tube 12 entrains there-with exfoliated fetal tissue which have collected in the region of the internal os of the uterus. When the saline solution and entrained cells have flowed back into the tube, the plunger is returned to its closed position (see FIG. 1) and the device is removed. The sample cells and solution may be removed from the device, cultured, and examined in a conventional manner.

A primary attribute of the device of this invention is sterility. The device and the internal area of the tube in particular are retained in a sterile condition until sampling occurs so that no external source of contamination can affect the sampled tissue. Moreover, the device can be used with little discomfort to the pregnant female and without adversely affecting the pregnancy. Because saline solution is first gently flowed into and then withdrawn from the region of the internal os, no undesirable scraping occurs, nor is an undesirable negative suction or pressure used to obtain cell samples.

Thus the present invention involves a device and method which may be safely employed during early stages of the pregnancy to obtain fetal cells for genetic diagnoses. The device is simple in design and manufacture, easy to use, and can be readily be employed to screen virtually every pregnancy.

We claim:

1. A sterile antenatal cell extracting device comprising:
    flexible, plastic tube means having a proximal end and a distal end adapted for cervical insertion into a pregnant female;
    flexible closure means comprising a flexible sleeve covering the proximal end of the tube means, with the plunger means passing through the sleeve;
    plunger means provided within the lumen of the tube means and passing through the closure means at the proximal end of the tube means being movable with respect to the tube means;
    valve means in association with the distal ends of the plunger means and of the tube means, movement of the plunger means with respect to the tube means causing the valve means to open and close the distal end of the tube means; and
    means for causing fluid to flow selectively into and out of the tube means when the valve means is open,
    whereby sterile antenatal cells may be extracted from the pregnant female.

2. A device, as claimed in claim 1, wherein the valve means comprises a ball fixed to the distal end of the plunger means.

3. A device, as claimed in claim 1, wherein the valve means comprises a ball fixed to the distal end of the plunger means, the diameter of the ball being larger than the diameter of the tube means whereby, when the plunger means is moved to its position with the ball flush adjacent the distal end of the tube, fluid cannot flow through the tube means.

4. A device, as claimed in claim 1, wherein the means for causing fluid to flow is a syringe.

5. A device, as claimed in claim 1, and further comprising means for controlling the degree of movement of the plunger with respect to the tube.

6. A sterile antenatal cell extracting device comprising:
    a flexible, plastic tube having a proximal end and a distal end adapted for cervical insertion into a pregnant female;

a flexible sleeve secured to the proximal end of the tube;

a plunger passing through the lumen of the tube and through the sleeve at the proximal end of the tube and extending from the tube at the distal end thereof;

a ball secured to the distal end of the tube and adapted to close the tube distally when positioned flush adjacent the distal end of the tube, the plunger being movable with respect to the tube in order to move the ball from the position wherein it closes the tube to a position wherein the tube is open and fluid may flow there through; and syringe means in fluid communication with the sleeve for causing fluid to flow selectively into and out of the tube when the ball is moved away from the distal end of the tube, whereby sterile antenatal cells may be extracted from the pregnant female.

7. A non-invasive method for obtaining sterile samples of viable antenatal human cells during the first trimester of pregnancy comprising the steps of:

inserting into the cervix of a pregnant female a sterilized antenatal cell extracting device comprising:

flexible, plastic tube means having a proximal end and a distal end adapted for cervical insertion;

flexible closure means provided for the proximal end of the tube means;

plunger means provided within the lumen of the tube means and passing through the closure means at the proximal end of the tube means, the plunger means being movable with respect to the tube means;

valve means in association with the distal ends of the plunger means and of the tube means, movement of the plunger means with respect to the tube means causing the valve means to open and close the distal end of the tube means;

means for causing fluid to flow selectively into and out of the tube means when the valve means is open;

moving the plunger means with respect to the tube means so as to open the valve means;

gently causing saline solution to flow through the tube means into the areas of the uterus adjacent to the distal end of the tube means;

thereafter causing such solution to return to the tube means with entrained sterile viable antenatal cells;

moving the plunger means so as to close the valve means; and removing the device from the pregnant female.

* * * * *